United States Patent [19]

McRae

[11] Patent Number: Plant 6,424

[45] Date of Patent: Nov. 29, 1988

[54] LILY NAMED CORAL PIXIE

[75] Inventor: Edward A. McRae, Boring, Oreg.

[73] Assignee: Melridge, Inc., Gresham, Oreg.

[21] Appl. No.: 18,917

[22] Filed: Feb. 25, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler

[57] ABSTRACT

A new variety of hybrid lily plant of short stature and bearing large clusters of medium sized, upright flowers particularly characterized by their 'old rose' gold accented coloration and the small number of tiny spots, the flowers being of excellent form and long persistence. The short stature of this plant and its moderately long, full leaves provide a color pattern and silhouette completely new in the upright Asiatic divisions of lilies making it especially suitable as a pot plant variety well suited to forcing and to mass commercial cultivation. This plant is highly resistant to disease and shows high tolerance of virus, making it an excellent garden plant, and its bulbs may be precooled and forced throughout the year for pot plant production.

1 Drawing Sheet

BACKGROUND OF THE NEW PLANT

This new variety of lily plant originated as a seedling selected from a group of seedlings planted by me at Sandy, Oreg., and obtained from a hybrid developed by me at Sandy, Oreg., by crossing a short, pink, Asiatic hybrid seedling as the seed parent and the clonal cultivar 'Peachblush' (U.S. Plant Pat. No. 4,334) as the pollen parent, my object being the production of lilies in shades of pink and peach well suited to forcing for pot plant production out-of-season.

The present seedling was selected by me for propagation and test because of its unusual flower coloration, its short stature, abundant foliage, and large number of flowers borne as a raceme on a single stem. This selected seedling was propagated by me at Sandy, Oreg., by bulb-scale propagation and by natural propagation from bulblets and successive generations produced in the same manner have demonstrated that the novel characteristics of this new plant hold true from generation to generation and appear to be firmly fixed.

Work with this new variety has demonstrated that it remains short and is not overly susceptible to bud abortion when forced into flower out-of-season as a pot plant from bulbs dug at the appropriate time and properly precooled; October-dug bulbs, properly precooled and potted in January, will flower under glass in western Oregon, with no supplemental lighting and at moderate greenhouse temperatures, in an average of 75 to 85 days.

DESCRIPTION OF THE DRAWING

My new variety of lily plant is illustrated by the accompaying photographic drawing, which shows buds and open blooms in full color, showing the flower form, the tepal arrangement, and the novel and distinctive old rose, gold accented, inconspicuously spotted coloration, the colors shown being as nearly true to those herein specified as is reasonably possible to obtain by professional photographic procedures.

DESCRIPTION OF THE NEW VARIETY

The following is a detailed description of my new variety of Asiatic hybrid lily based upon observations of plants grown at Sandy, Oreg., during the middle of 1986, the nomenclature being according to The International Lily Register (The Royal Horticultural Society of London, England, 2nd Edition, 1969) and the color designations are according to The R.H.S. Colour Chart published by The Royal Horticultural Society in 1966.

THE PLANT

Origin: Seedling.

Parentage:

*Seed parent.*—A pink, Asiatic hybric Lilium seedling.

*Pollen parent.*—'Peachblush' (U.S. Plant Pat. No. 4,334).

Classification:

*Botanic.*—Division I-A, upright Asiatic hybrid lily, according to the Horticultural Classification of Lilies by The Royal Horticultural Society of London.

*Commercial.*—Hybrid Lilium clone.

Form: Single stem, erect and stately.

Height: About 35 to 50 cm. for stems produced by glasshouse forcing of bulbs of about 12 to 18 cm. in circumference, provided that the light levels are adequate. 'Stretching' may result from low light levels.

Growth: Vigorous and upright.

Foliage:

*Quantity.*—Abundant.

*Size of leaf.*—About 8 to 14 cm. long and about 0.5 to 0.8 cm. wide.

*Shape of leaf.*—Lanceolate with acuminate tip and entire margins.

*Texture.*—Leathery.

*Aspect.*—Glossy and lightly pubescent.

*Color.*—Dark green, but lighter on the lower side.

The bulb:

*Size.*—Varying, ranging to about 25 cm. in circumference in commercial use.

*Color.*—White.

THE BUD

Form: Long ovoid with obtuse tip and base.

Size: About 8 to 9 cm. long and about 5 cm. in circumference just prior to opening.

Opening rate: The bud opens slowly, taking about one hour in response to morning light.

Color: Soft to medium pink (RHS 51D) with a flush of green along the midribs and at the tip prior to opening and as the tepals begin to unfurl.

Peduncle:

*Length.*—About 4 to 6 cm., in average, but may elongate if light levels are too low or if the bulbs have been improperly stored prior to forcing.

*Color.*—Dark green.

THE FLOWER

Blooming habit: Once annually, flowering profusely in midseason.

Size: The flowers average about 13 to 15 cm. in diameter.

Borne: In a single compact raceme having 6 to 12 buds from a bulb of about 12 to 16 cm. in circumference.

Shape: Cup-shaped when first opening and flattening as the tepals recurve by the second day.

Tepalage: Normal, with six tepals in hexagonal arrangement and slightly overlapping.

*Tepal size.*—The outer tepals average about 3 cm. wide and the inner tepals average about 3.5 to 4 cm. wide. The inner tepals meet base-to-base.

*Color.*—The flowers are distinguished by their broad-tepalled form and thick substance, and particularly by their deep pink coloration created by purple-pink pigments in the upper cell layers, covering soft golden orange pigments in the central call layers; this combination appears to the eye to be red, RHS 54B-C, deepening to RHS 54A along the tepal margins and at the tips. A flush of gold, RHS 23C-D, about 1 cm. wide, extends down the midrib about 1 to 2 cm. from the nectaries. The nectaries are soft peach overlaid with white pubescence.

*Spotting.*—Each of the tepals has about 50 tiny magenta spots at the tepal base parallel with the nectaries and collectively the tepal spots form a dainty ring encircling the center of the flower.

*Longevity.*—The tepals stay on the stems about three weeks.

Pedicel:

*Length.*—About 4 to 8 cm., in average.

*Form.*—Sturdy and ascending up to about 60 degrees from the horizontal.

*Color.*—Dark green and lightly pubescent.

Color changes: The flowers may become slightly more apricot-toned under conditions of great heat and strong light. With very cool temperatures and moderate light levels, the flowers may become more pink-toned.

Aspect: The flower is shiny.

Disease resistance: As observed in western Oregon, the flower and plant are resistant to Fusarium bulb rot and Botrytis blight.

Lasting quality: The flower is very long lasting.

REPRODUCTIVE ORGANS

Stamens:

*Number.*—Six, in arrangement typical of genus Lilium.

*Pollen and anthers (dehisced).*—Greyed orange, RHS 169A.

*Filaments.*—Length: About 5 cm. Color: Soft cream to pink.

Pistil:

*Number.*—One.

*Style.*—Length: About 5 cm.

*Stigma.*—Size: Large. Color: Deep plum.

Character of ovary: The ovary has the characteristics of the genus Lilium.

THE PLANT

Fertility: The fruit is fertile.

Shape: Ovoid.

Color at maturity: Soft brown, somtimes overlaid with soft plum.

This new lily variety most closely resembles the variety 'Peachblush' (U.S. Plant Pat. No. 4,334) but it has a deeper pink and less peach coloration with a dainty ring of tiny spots encircling the center of the flower, a more complact inflorescence with shorter pedicels, less height, and more abundant and narrower leaves. The new plant also resembles 'Peach Pixie', copending Plant patent application Ser. No. 07/018,919, but it has a deeper 'old rose' pink coloration rather than a peach-pink coloring.

I claim:

1. The new and distinctive variety of Asiatic hybrid lily and parts thereof, substantially as herein shown and described, characterized by its gold accented, 'old rose' colored flowers with their dainty ring of tiny spots, the excellence of its flower form, and its versatility both as a garden plant and as a pot plant variety well suited to forcing into flower out-of-season.

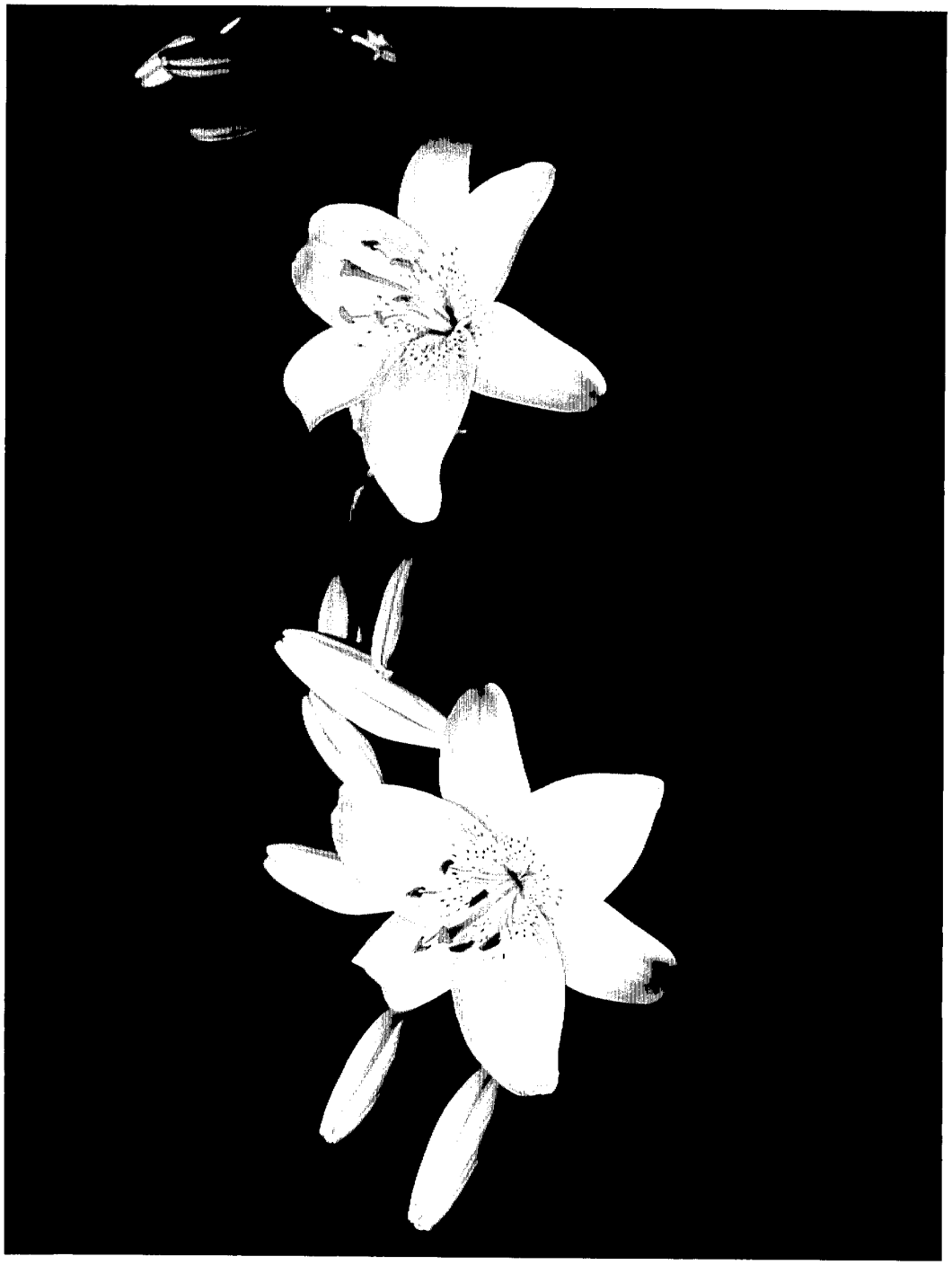

* * * * *